United States Patent [19]
Akamatsu et al.

[11] Patent Number: 5,788,990
[45] Date of Patent: Aug. 4, 1998

US005788990A

[54] WATER-REPELLENT POWDER AND MANUFACTURE OF THE SAME

[75] Inventors: Shoji Akamatsu; Toshinori Watanabe, both of Chiba Prefecture, Japan

[73] Assignee: Dow Corning Toray Silicone Co., Ltd., Tokyo, Japan

[21] Appl. No.: 574,886

[22] Filed: Dec. 19, 1995

[30] Foreign Application Priority Data

Dec. 21, 1994 [JP] Japan ................................. 6-335682

[51] Int. Cl.$^6$ ................. C09C 3/12; C09C 1/02; C01D 13/00

[52] U.S. Cl. ................. 424/489; 523/210; 524/450; 524/791; 428/403; 428/404; 428/405; 428/407

[58] Field of Search ................. 424/489; 523/210; 524/450, 791; 428/403, 404, 405, 407

[56] References Cited

U.S. PATENT DOCUMENTS

| | | | |
|---|---|---|---|
| 4,513,053 | 4/1985 | Chen et al. | 428/221 |
| 5,162,395 | 11/1992 | Yamazaki et al. | 523/209 |
| 5,192,615 | 3/1993 | McDougall et al. | 428/402.24 |
| 5,204,183 | 4/1993 | McDougall et al. | 428/402.24 |
| 5,362,517 | 11/1994 | Flesher et al. | 427/22 |

FOREIGN PATENT DOCUMENTS

| | | |
|---|---|---|
| 043264 | 5/1979 | Japan . |
| 56-043264 | 10/1981 | Japan . |

*Primary Examiner*—Nathan M. Nutter
*Attorney, Agent, or Firm*—Alex Weitz

[57] ABSTRACT

There is disclosed a water-repellent powder which is prepared by (A) coating the surface of a deliquescent powder with a curable silicone-based formation agent; and (B) curing said formation agent to provide a silicone-based cured film on said powder. Preferably, the deliquescent powder is selected from the group consisting of ammonium acetate, potassium acetate and sodium acetate.

6 Claims, No Drawings

WATER-REPELLENT POWDER AND MANUFACTURE OF THE SAME

FIELD OF THE INVENTION

The present invention concerns a water-repellent powder and a method for manufacturing the same. Specifically, it concerns a water-repellent powder that has adjustable deliquescent properties.

BACKGROUND OF THE INVENTION

Powders such as calcium chloride, ammonium acetate, potassium acetate and sodium acetate readily deliquesce in moist air, and the range of use of such substances is thus limited. In addition, even if the surface of these deliquescent powders is made water repellent by coating the surfaces with non-curing silicone, the water repellence does not last, and the deliquescent properties of the substances cannot be adjusted.

SUMMARY OF THE INVENTION

The objective of the present invention is to provide a water-repellent powder having adjustable deliquescent properties and a method for manufacturing this powder. The invention, therefore, relates to a water-repellent powder prepared by (A) coating a surface of a deliquescent powder with a curable silicone-based formation agent; and (B) curing said formation agent to provide a silicone-based cured film on the surface of said deliquescent powder.

The present invention has been disclosed in Japanese Laid Open Patent Application Number Hei 6-335682, the full disclosure of which is hereby incorporated by reference.

DETAILED DESCRIPTION OF THE INVENTION

The water-repellent powder of the present invention is produced by coating the surface of a deliquescent powder with a silicone-based cured film. There are no particular limitations on the type of deliquescent powder and examples include calcium chloride hexahydrate, sodium chloride, sodium hydroxide, sodium perchlorate monohydrate, calcium nitrate, calcium nitrite, hydrates of iron(II) sulfate, iron chloride tetrahydrate, iron(II) chloride hexahydrate, iron(II) nitrate hexahydrate, iron(II) nitrate nonahydrate, copper nitrate trihydrate, copper nitrate hexahydrate, magnesium nitrate hexahydrate, sodium phosphate dihydrate, sodium hypophosphite monohydrate, potassium pyrophosphate, sodium hexametaphosphate and other inorganic salts; as well as ammonium acetate, potassium acetate, sodium acetate and other organic carboxylates. In the water-repellent powder of the present invention, the deliquescent powders that are preferred are selected from a group consisting of ammonium acetate, potassium acetate and sodium acetate. There are no particular limitations on the grain diameter or form of the deliquescent powder, but in terms of handling ease, an average grain diameter in the range of 10 μm to 2 mm is preferred.

There are no particular limitations on the form or film thickness of the silicone-based cured film and examples include elastomeric and varnish-like forms. In general, because the silicone-based cured film has appropriate moisture permeability characteristics, the deliquescent powder which is the core of the water-repellent powder of the present invention does not lose its intrinsic deliquescent characteristics, and it is thus possible to freely adjust the deliquescent characteristics of the substance. Examples of silicone-based cured films include cured films made of silicone resins having silanol groups or alkoxy groups bonded to silicon atoms, cured films formed from diorganopolysiloxanes having silanol groups or alkoxy groups bonded to silicon atoms, cured films made of silicone resins that have been modified with epoxy resin, polyester resin, phenol resin and other organic resins, and cured films made of organotrialkoxysilanes or partially hydrolyzed condensation products thereof. In the water-repellent powder of the present invention, there are no particular restrictions on the weight of the silicone-based cured film, but from the standpoint of practicality, a range of about 0.01–30 parts by weight with respect to 100 parts by weight of the deliquescent powder is preferred, with a range of 0.1–10 parts by weight being particularly desirable. The weight should be in this range because the deliquescent characteristics of the resulting water-repellent powder become problematic if the silicone-based cured film is present in an amount that is less than about 0.01 part by weight with respect to 100 parts by weight of the deliquescent powder. In addition, the deliquescent characteristics of the resulting water-repellent powder will be difficult to manifest if the amount is in excess of about 30 parts by weight.

The manufacturing method of the present invention is characterized in that the curable formation agent for the silicone-based cured film is cured during or after application of the formation agent to the surface of the deliquescent powder. The type of deliquescent powder is generally described above, but in the manufacturing method of the present invention, it is preferable, in terms of practicality, for the deliquescent powder to be at least one organic carboxylate selected from ammonium acetate, potassium acetate or sodium acetate. Although there are no particular limitations on the grain diameter, form, etc., of the deliquescent powder, it is desirable for the average grain diameter to be in the range of 10 μm to 2 mm from the standpoint of handling ease. In addition, there are no particular limitations on the constitution of the curable agent for forming the silicon-based cured film. Examples of such agents include a composition composed solely of silicone resin having silanol groups or alkoxy groups bonded to silicon atoms, a composition composed of this silicone resin and a curing agent and/or curing catalyst, a composition composed of a diorganopolysiloxane having silanol groups or alkoxy groups bonded to silicon atoms along with a curing agent and/or curing catalyst, a composition composed of organohydrogen polysiloxane, a composition composed solely of silicone resin modified with an organic resin such as epoxy resin, polyester resin or phenol resin, a composition composed of this silicone resin and a curing agent and/or curing catalyst and a composition composed solely of an organotrialkoxysilane and/or a partial hydrolysis product thereof.

Examples of methods for preparing the silicone resin having silanol groups or alkoxy groups bonded to silicon atoms include methods where a tetramethoxysilane, tetraethoxysilane or tetrapropoxysilane or other tetraalkoxysilane and/or methyltrimethoxysilane, methyltriethoxysilane, ethyltrimethoxysilane, vinyltrimethoxysilane, phenyltrimethoxysilane, phenyltriethoxysilane or other organotrialkoxysilane is subjected to hydrolysis and condensation along with, as necessary, dimethyldimethoxysilane, dimethyldiethoxysilane, methylvinyldimethoxysilane, methylphenyldimethoxysilane, methylphenyldiethoxysilane or other diorganodialkoxysilane and/or trimethylmethoxysilane, trimethylethoxysilane, dimethylvinylmethoxysilane, phenyltrimethoxysilane or other triorganoalkoxysilane; and methods wherein tetrachlorosilane and/or methyltrichlorosilane, ethyltrichlorosilane, vinyltrichlorosilane, phenyltrichlorosilane or other organotrichlorosilane is subjected to hydrolysis and condensation along with, as necessary, dimethyldichlorosilane, methylvinyldichlorosilane, methylphenyldichlorosilane, diphenyldichlorosilane and other diorganodichlorosilanes and/or trimethylchlorosilane, triethylchlorosilane, dimethylvinylchlorosilane, dimethylphenylchlorosilane or other triorganochlorosilane.

Although compositions composed only of such silicone resins can be used as the agent for forming the silicone-based film of the present invention, it is necessary to heat the composition to a relatively high temperature in order to cure said formation agent. For this reason, it is desirable to blend a curing agent and/or curing catalyst with this silicone resin. Examples of curing agents include methyltrimethoxysilane, ethyltrimethoxysilane, vinyltrimethoxysilane, phenyltrimethoxysilane and other organotrialkoxysilanes, methyltris(isopropoxy)silane, vinyltris(isopropenoxy)silane and other organotrialkenoxysilanes, methyltriacetoxysilane, vinyltriacetoxysilane and other organotriacetoxysilanes, methyltris(dimethylketoxime)silane, ethyltris(methylethylketoxime)silane, vinyltris(methylethylketoxime)silane and other organotrioxime silanes. The blend amount of such curing agents is preferably in the range of about 0.1–20 parts by weight with respect to 100 parts by weight of the aforementioned silicone resin. In addition, examples of curing catalysts include tin stearate, tin laurate, tin oleate and other organic metal salts; dibutyltin diacetate, dibutyltin dilaurate, dibutyltin dioctoate, dimethyltin dimonooleate, dioctyltin dilaurate, diphenyltin diacetate and other organic tin compounds, tetrabutyl titanate, diisopropoxybis(acetylacetonate)titanium, diisopropoxybis(ethylacetoacetate)titanium and other organic titanium compounds. The blended amount of such curing catalysts is preferably in the range of about 0.01–10 parts by weight with respect to 100 parts by weight of the aforementioned silicone resin.

Examples of the diorganopolysiloxane having silanol groups or alkoxy groups bonded to silicon atoms include dimethylpolysiloxanes wherein both terminals of the molecular chain are blocked with trimethoxysiloxy groups, copolymers of dimethylphenylsiloxane and dimethylsiloxane wherein both terminals of the molecular chain are blocked with trimethoxysiloxy groups, dimethylpolysiloxane wherein both terminals of the molecular chain are blocked with methyldimethoxysiloxy groups, copolymers of methylphenylsiloxane and dimethylsiloxane wherein both terminals of the molecular chain are blocked with methyldimethoxysiloxy groups, dimethylpolysiloxane wherein both terminals of the molecular chain are blocked with trimethoxysilylethyl groups, dimethylpolysiloxane wherein both terminals of the molecular chain are blocked with silanol groups, and copolymers of methylphenylsiloxane and dimethylsiloxane wherein both terminals of the molecular chain are blocked with silanol groups. In addition, the blend amount of such curing agents is preferably in the range of about 0.1–20 parts by weight with respect to 100 parts by weight of the aforementioned diorganopolysiloxane. Examples of curing catalysts include the same organometallic salts, organotin compounds, and organotitanium compounds described above, and the blend amount of such curing catalysts is preferably in the range of about 0.01–10 parts by weight with respect to 100 parts by weight of the aforementioned diorganopolysiloxane.

In addition, the organohydrogenpolysiloxane is exemplified by trimethylsiloxy-endblocked methylhydrogenpolysiloxane, trimethylsiloxy-endblocked dimethylsiloxane-methylhydrogensiloxane copolymer, and silanol-endblocked methylhydrogenpolysiloxane.

In addition, examples of methods for preparing the silicone resin that is modified with an organic resin such as epoxy resin, polyester resin or phenol resin include methods wherein an organic resin such as epoxy resin, polyester resin or phenol resin is heated along with the aforementioned silicone resin having alkoxy groups or silanol groups bonded to silicon atoms in the presence of a condensation catalyst such as tetraisopropyl titanate or tetrabutyl titanate.

Although compositions composed only of silicone resin modified with such organic resins may be used as the agent for forming the silicone-based cured film, it is necessary to heat such a composition to a relatively high temperature in order to cure the formation agent. For this reason, it is preferable to blend a curing agent and/or curing catalyst with the silicone resin. Examples of curing agents include phthalic anhydride, hexahydrophthalic anhydride, trimellitic anhydride, tetrahydrophthalic anhydride, pyromellitic anhydride, dodecylsuccinic anhydride, benzophenone tetracarboxylic anhydride, butane tetracarboxylic anhydride and other anhydrides, ethylenediamine, diethylenetriamine, triethylenetetramine, diethylaminopropylamine, N-aminoethylpiperazine, bis(4-amino-3-methylcyclohexyl)methane, m-xylyleneamine, methanediamine, 3,9-bis(3-aminopropyl)-2,4,8,10-tetraoxaspyro[5.5]undecane and other amine compounds, 3-aminopropyltrimethoxysilane, 3-aminoxypropyltriethoxysilane, 3-(2-N-aminoethyl)aminopropyltrimethoxysilane, 3-(2-aminoethyl)aminopropyltriethoxysilane and other amino group-containing silane compounds, diethylenetriamine addition products of epoxy resins, ethylene oxide adducts of amines, cyanoethylated polyamines and other modified aliphatic polyamines, phenol, bisphenol A, bisphenol F, tetrabromobisphenol A, cresol and other phenol compounds and xylene resins. The blend amount of such curing agents is preferably in the range of about 0.1–100 parts by weight with respect to 100 parts by weight of the aforementioned silicone resin. In addition, examples of curing catalysts include ethanol, isopropanol, butanol and other alcohols, the aforementioned amine compounds, the aforementioned phenol compounds, triphenylphosphine and other phosphine compounds and 2-phenylimidazole and other imidazole compounds.

Examples of organotrialkoxysilanes include methyltrimethoxysilane, ethyltrimethoxysilane, propyltrimethoxysilane, butyltrimethoxysilane, vinyltrimethoxysilane, allyltrimethoxysilane, phenyltrimethoxysilane, methyltriethoxysilane, vinyltriethoxysilane, allyltriethoxysilane, 3-aminopropyltrimethoxysilane, N-(2-aminoethyl)-3-aminopropyltrimethoxysilane, 3-glycidoxypropyltrimethoxysilane, 2-(3,4-epoxycyclohexyl)ethyltrimethoxysilane and 3-methacryloxypropyltrimethoxysilane.

In order to adjust the solids content or viscosity, and thus control the film thickness of said formation agent that is coated onto the surface of the deliquescent powder, methanol, ethanol, propanol and other alcohol-based organic solvents, toluene, xylene and other aromatic organic solvents, hexane, heptane, octane and other aliphatic hydrocarbon-based organic solvents, acetone, methyl ethyl ketone, methyl isobutyl ketone and other ketone-based organic solvents, methyl ethyl ether, diethyl ether, tetrahydrofuran and other ether-based organic solvents, and methyl acetate, ethyl acetate, propyl acetate and other ester-based organic solvents, can be blended with these agents for forming the silicone-based cured film.

Although there are no particular limitations on the blend amount of this agent for forming the silicone-based cured film in the method of the present invention, in terms of practicality, an amount should be used so that the resulting silicone-based cured film produced by curing said formation agent is in the range of about 0.01–30 parts by weight with respect to 100 parts by weight of the deliquescent powder, with a range of 0.1–10 parts by weight being particularly desirable. If an amount of agent for forming the silicone-based cured film is used that gives a silicone-based cured film whose weight is less than 0.01 part by weight with respect to 100 parts by weight of the deliquescent powder, it will be difficult to adjust the deliquescent characteristics of the water-repellent powder, whereas if said formation agent is used in such an amount that this weight is greater than 30 parts by weight, it will be difficult to manifest the deliquescent properties of the resulting water-repellent powder, and in addition, the amount of the cured powder that is composed solely of said formation agent will be greatly increased.

There are no particular restrictions on the method for coating the agent in forming the silicone-based cured film on the surface of the deliquescent powder. Examples include methods wherein the deliquescent powder and the agent for forming the silicone-based cured film are mixed uniformly by means of a mixing apparatus such as a Henschel mixer, ribbon blender, super mixer or ball mill, and methods wherein the agent for forming the silicone-based cured film is spray-coated onto said powder as the deliquescent powder is allowed to float freely in a fluidized bed.

Examples of the method for curing the agent for forming the silicone-based cured film coated onto the surface of the deliquescent powder include methods wherein heating is carried out in an oven or fluidized bed at about 50°–250° C., with 100°–200° C. being preferred, after or during the coating of the surface of said powder with said formation agent.

The water-repellent powder of the present invention is produced by adjusting the deliquescent properties intrinsic to the deliquescent powder which is the core of the powder, thus making the substance easy to handle and amenable to use as a moisture absorbent or antifreeze agent.

EXAMPLES

The water-repellent powder and method for its manufacture according to the present invention is described in additional detail below by means of application examples. In the application examples, the viscosity is the value measured at 25° C.

Reference Example 1

Eight moles of methyltrichlorosilane and 2 moles of dimethyldichlorosilane were introduced into a system of water and toluene under vigorous agitation, and these substances were allowed to undergo cohydrolysis and condensation reactions. A 50 wt % toluene solution of silicone resin containing 0.5 wt % silanol was thus prepared. To 100 parts by weight of this solution were added 10 parts by weight of methyltrimethoxysilane and 2 parts by weight of dibutyltin dilaurate, and the substances were mixed to homogeneity to prepare the formation agent (A) for the silicone-based film.

Reference Example 2

Eight parts by weight of tris(methylethylketoxime) methyl-silane, 1 part by weight of dibutyltin dilaurate and 60 parts by weight of xylene were mixed to homogeneity with 40 parts by weight of dimethylpolysiloxane with a viscosity of 130 P wherein both terminals of the molecular chain were blocked with silanol groups to produce a formation agent (B) for a silicone-based film.

Reference Example 3

One hundred and sixty parts by weight of Novolak epoxy resin (trade name Epikote 1001, manufactured by Yuka Shell Epoxy K.K.) and 240 parts by weight of a partial hydrolysis product of methyltrimethoxysilane (equivalent mole numbers of methyl groups and methoxy groups in the hydrolysis product) were allowed to undergo a condensation reaction in 600 parts by weight of xylene to produce a 40 wt % xylene solution of silicone resin modified with epoxy resin having a viscosity of 60 cP. Six parts by weight of aminoethylaminopropyl trimethoxysilane was added to 100 parts by weight of this solution, and this combination was mixed until uniform to produce a formation agent (C) for a silicone-based cured film.

Application Example 1

Fifty mL of toluene and 2 g of formation agent (A) for the silicone-based cured film prepared in Reference Example 1 were introduced into a 300 -mL separatory flask equipped with a stirring device and a condenser, and the contents were stirred until uniform. To this solution were added 100 g of potassium acetate powder with an average grain diameter of 100 μm, and the toluene was removed under ambient pressure as the mixture was stirred until uniform. At the point when the toluene was almost completely eliminated, the contents were removed to a vat, and this vat was heated for 1 h in an oven at 150° C. to prepare a water-repellent powder.

Upon transferring this powder into water at 25° C., the powder dissolved after floating in the water for about 3 h. In addition, this powder was washed with toluene, and was introduced into water at 25° C., and in like fashion, the powder dissolved after floating in the water for about 3 h. Moreover, deliquescence occurred after about 3 h when the powder was placed in 55% RH at 25° C.

Application Example 2

A water repellent powder was prepared in the same manner as in Application Example 1, with the exception that 2 g of methylhydrogenpolysiloxane having a viscosity of 20 cP, wherein both molecular terminals were blocked with trimethylsiloxy groups (silicon-bonded hydrogen atom content =1.58) was used instead of the formation agent (A).

Upon placing this powder in water at 25° C., dissolution occurred about 3 h after floating in the water. In addition, when the powder was introduced into water at 25° C. after having been washed with toluene, dissolution occurred in like manner after floating in the water for about 3 h. Deliquescence occurred after about 3 h when the powder was placed in 55% RH (relative humidity) at 25° C.

Application Example 3

Twenty g of sodium acetate powder with an average grain diameter of 100 μm and 5 g of the formation agent (B) for the silicone-based cured film prepared in Reference Example 2 were blended in a Henschel mixer, and the two were mixed until uniform. The mixture was then heated for 1 h in an oven at 150° C. to prepare a water-repellent powder.

Upon introducing this powder into water at 25° C., dissolution occurred after floating in the water for 3 h. In addition, when the powder was introduced into water at 25° C. after having been washed with toluene, dissolution occurred in like manner after floating in the water for about 3 h. Deliquescence occurred after about 3 h when the powder was placed in 55% RH at 25° C.

Application Example 4

Five hundred g of sodium acetate powder with an average grain diameter of 100 μm was fluidized at a temperature of 120° C., and 50 g of the formation agent (C) for the silicone cured film prepared in Reference Example 3 was spray coated over a period of 1 hour. The composition was then heated for 1 hour in an oven at 120° C. to prepare a water-repellent powder.

Upon introducing this powder into water at 25° C., dissolution occurred after the powder floated in the water for 3 h. In addition, when the powder was introduced into water at 25° C. after having been washed with toluene, dissolution occurred in like manner after floating in the water for about 3 h. Deliquescence occurred after about 3 h when the powder was placed in 55% RH at 25° C.

Application Example 5

A water-repellent powder was prepared in the same manner as in Application Example 1, with the exception that 2 g of methyltrimethoxysilane was added instead of the formation agent (A) for the silicone cured film in Application Example 1.

Upon introducing this powder into water at 25° C., dissolution occurred after floating in the water for 3 h. In addition, when the powder was introduced into water at 25° C. after having been washed with toluene, dissolution occurred in like manner after floating in the water for about 3 h. Deliquescence occurred after about 3 h when the powder was placed in 55% RH at 25° C.

Comparative Example 1

The potassium acetate powder used in Application Example 1 was introduced into water at 25° C., and immediately dissolved in the water. Upon placing the powder in 55% RH at 25° C., dissolution occurred immediately.

Comparative Example 2

A water-repellent powder was prepared in the same manner as in Application Example 1, with the exception that 2 g of dimethylpolysiloxane, with a viscosity of 100,000 cP and both molecular terminals blocked with trimethylsiloxy groups, was used instead of the formation agent (A) for the silicone cured film in Application Example 1.

Upon introducing this powder into water at 25° C., dissolution occurred after floating in the water for about 10 min. Deliquescence occurred after about 1 h when the powder was placed in 55% RH at 25° C.

In addition, when this powder was immersed in water at 25° C. after having been washed in toluene, dissolution rapidly occurred. Deliquescence occurred immediately when this powder was placed in 55% RH at 25° C.

That which is claimed is:

1. A water-repellent powder prepared by
   (A) coating a surface of a deliquescent powder selected from the group consisting of
      calcium chloride hexahydrate, sodium chloride, sodium perchlorate monohydrate, calcium nitrate, calcium nitrite, hydrates of iron(II) sulfate, iron chloride tetrahydrate, iron(II) chloride hexahydrate, iron(II) nitrate hexahydrate, iron(II) nitrate nonahydrate, copper nitrate trihydrate, copper nitrate hexahydrate, magnesium nitrate hexahydrate, sodium phosphate dihydrate, sodium hypophosphite monohydrate, potassium pyrophosphate, sodium hexametaphosphate, ammonium acetate, potassium acetate and sodium acetate with a curable silicone-based formation agent; and
   (B) curing said formation agent to provide a silicone-based cured film on the surface of said deliquescent powder, such that 0.01 to 30 parts by weight of said silicone-based cured film is present for each 100 parts by weight of said deliquescent powder and said water-repellent powder has adjustable deliquescent properties.

2. The water-repellent powder according to claim 1, wherein said deliquescent powder is selected from the group consisting of ammonium acetate, potassium acetate and sodium acetate.

3. The water-repellent powder according to claim 2, wherein 0.1 to 10 parts by weight of said silicone-based cured film is present for each 100 parts by weight of said deliquescent powder.

4. A method for preparing a water-repellent powder, said method comprising
   (A) coating a surface of a deliquescent powder selected from the group consisting of
      calcium chloride hexahydrate, sodium chloride, sodium perchlorate monohydrate, calcium nitrate, calcium nitrite, hydrates of iron(II) sulfate, iron chloride tetrahydrate, iron(II) chloride hexahydrate, iron(II) nitrate hexahydrate, iron(II) nitrate nonahydrate, copper nitrate trihydrate, copper nitrate hexahydrate, magnesium nitrate hexahydrate, sodium phosphate dihydrate, sodium hypophosphite monohydrate, potassium pyrophosphate, sodium hexametaphosphate, ammonium acetate, potassium acetate and sodium acetate with a curable silicone-based formation agent; and
   (B) curing said formation agent to provide a silicone-based cured film on the surface of said deliquescent powder, such that 0.01 to 30 parts by weight of said silicone-based cured film is present for each 100 parts by weight of said deliquescent powder and said water-repellent powder has adjustable deliquescent properties.

5. The method according to claim 4, wherein said deliquescent powder is selected from the group consisting of ammonium acetate, potassium acetate and sodium acetate.

6. The method according to claim 5, wherein 0.1 to 10 parts by weight of said silicone-based cured film is present for each 100 parts by weight of said deliquescent powder.

* * * * *